United States Patent [19]

Levy

[11] E Patent Number: Re. 32,983

[45] Reissued Date of Patent: Jul. 11, 1989

[54] BALLOON AND MANUFACTURE THEREOF

[75] Inventor: Stanley B. Levy, Wilmington, Del.

[73] Assignee: E. I. Du Pont de Nemours and Company, Wilmington, Del.

[21] Appl. No.: 914,108

[22] Filed: Oct. 1, 1986

Related U.S. Patent Documents

Reissue of:

[64] Patent No.: 4,490,421
Issued: Dec. 25, 1984
Appl. No.: 510,812
Filed: Jul. 5, 1983

[51] Int. Cl.[4] ..... A61M 29/02

[52] U.S. Cl. ..... 428/36.92; 128/344; 156/244.13; 264/573; 428/480; 428/910; 604/96

[58] Field of Search ..... 428/35, 480, 482, 910, 428/35.5, 36.92; 128/344, 325; 604/96-103; 264/573; 156/244.13

[56] References Cited

U.S. PATENT DOCUMENTS

| | | | |
|---|---|---|---|
| 3,141,912 | 8/1964 | Goldman et al. | 264/95 |
| 3,432,591 | 10/1966 | Heffelfinger | 264/289 |
| 3,627,579 | 12/1971 | Heffelfinger | 117/236 |
| 3,733,309 | 5/1973 | Wyeth et al. | 215/16 |
| 3,865,666 | 2/1975 | Shoney | 264/248 |
| 4,093,484 | 6/1978 | Harrison et al. | 156/244.13 |
| 4,154,244 | 5/1979 | Becker et al. | 128/349 B |
| 4,254,774 | 3/1981 | Boretos | 128/348 |
| 4,256,789 | 3/1981 | Suzuki et al. | 428/35 |
| 4,367,747 | 1/1983 | Witzel | 128/344 |
| 4,411,055 | 10/1983 | Simpson et al. | 29/447 |
| 4,456,000 | 6/1984 | Schjeldahl et al. | 604/49 |
| 4,531,943 | 7/1985 | Van Tassel et al. | 128/658 |
| 4,531,997 | 7/1985 | Johnston | 428/192 |
| 4,587,975 | 3/1986 | Salo et al. | 128/693 |
| 4,646,742 | 3/1987 | Packard et al. | 604/102 |

FOREIGN PATENT DOCUMENTS

| | | | |
|---|---|---|---|
| 2000406 | 9/1969 | France . | |
| 57-48377 | 10/1982 | Japan | 264/566 |
| 1253272 | 11/1971 | United Kingdom . | |
| 2011307 | 7/1979 | United Kingdom . | |

OTHER PUBLICATIONS

"Nonoperative Dilatation of Coronary-Artery Stenosis-Percutaneous Transluminal Coronary Angioplasty", The New England Journal of Medicine, vol. 301, No. 2, pp. 61-68, Jul. 12, 1979, Gruntzig et al.

Jungnickel, Progr. Colloid Polym Sci. 67, 1159-60 (1980).

*Primary Examiner*—Ellis P. Robinson
*Assistant Examiner*—James J. Seidleck

[57] ABSTRACT

Polymeric balloon having a burst pressure of at least 200 psi (1.4 MPa) and a radial expansion beyond nominal inflated diameter of less than 5% at 200 psi (1.4 MPa).

19 Claims, 2 Drawing Sheets

BALLOON AND MANUFACTURE THEREOF

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to balloon catheters which are especially useful in medical dilation procedures.

2. Background

In "Nonoperative Dilation of Coronary-Artery Stenosis—Percutaneous Transluminal Coronary Angioplasty", The New England Journal of Medicine, Vol. 301, No. 2, pages 61-68, July 12, 1979, Grüntzig et al. disclose an improved technique for the use of a dilating catheter to relieve arterial stenosis. According to Grüntzig et al. the technique of transluminal angioplasty for the treatment of atherosclerotic obstruction of the femoral artery was first introduced in 1964 by Dotter and Judkins.

Balloon catheters are not limited in their use to the relief of arterial stenosis but have been found useful in many medical applications involving not only insertion into blood vessels but also involving insertion into a variety of body cavities.

Although medical procedures using balloon catheters are still in the exploratory stage, particularly in the United States, considerable art is already available on the use of balloon catheters and their fabrication. Representative of such art are U.S. Pat. Nos. 4,093,484; 4,154,244; and 4,254,774. Balloons can be made from a variety of known materials which are generally of the thermoplastic polymeric type. Included among the known materials disclosed in the aforesaid patents are ethylene-butylene-styrene block copolymers admixed with low molecular weight polystyrene and, optionally, polypropylene, and similar compositions employing butadiene or isoprene in place of the ethylene and butylene; poly(vinyl chloride); polyurethanes; copolyesters; thermoplastic rubbers; siliconepolycarbonate copolymers; and ethylene-vinyl acetate copolymers.

It is an object of this invention to provide balloons which exhibit physical properties, for example, toughness, flexibility and tensile strength, superior to those exhibited by balloons known in the art. A further object is to provide balloons which, because of their superior physical properties, have thinner wall thickness than commonly used balloons. Another object is to provide such balloons which, because of their flexibility and thin walls, are more readily collapsible and more easily transportable in the body. It is also an object of the invention to provide such balloons which exhibit very little elongation or creep radially, collectively referred to herein as radial expansion, when inflated to the pressure necessary to perform the desired medical procedure. A further object is to provide such balloons which, if they burst under pressure, burst in the axial direction to give an axial rupture, thus ensuring atraumatic removal, it being well known that a balloon which bursts in a circumferential direction may provide fragments which either are removable only with difficulty or are not removable at all nonsurgically. A further object is to provide such balloons which, because of their superior physical properties, can be used in medical procedures with a greater probability of success. Another object is to provide such balloons which, because of their superior physical properties, can be used in medical procedures under conditions not currently achievable using commonly available balloons. Still another object is to provide a process for fabricating such balloons. These and other objects will become apparent from the following discussion of the invention.

DETAILED DESCRIPTION OF THE INVENTION

The invention resides in an improved balloon having an unusual combination of physical properties and which is especially useful in medical dilation procedures. The invention also resides in a process for fabricating such balloons, and in a dilatation balloon catheter comprising such an improved balloon.

Figure 2:
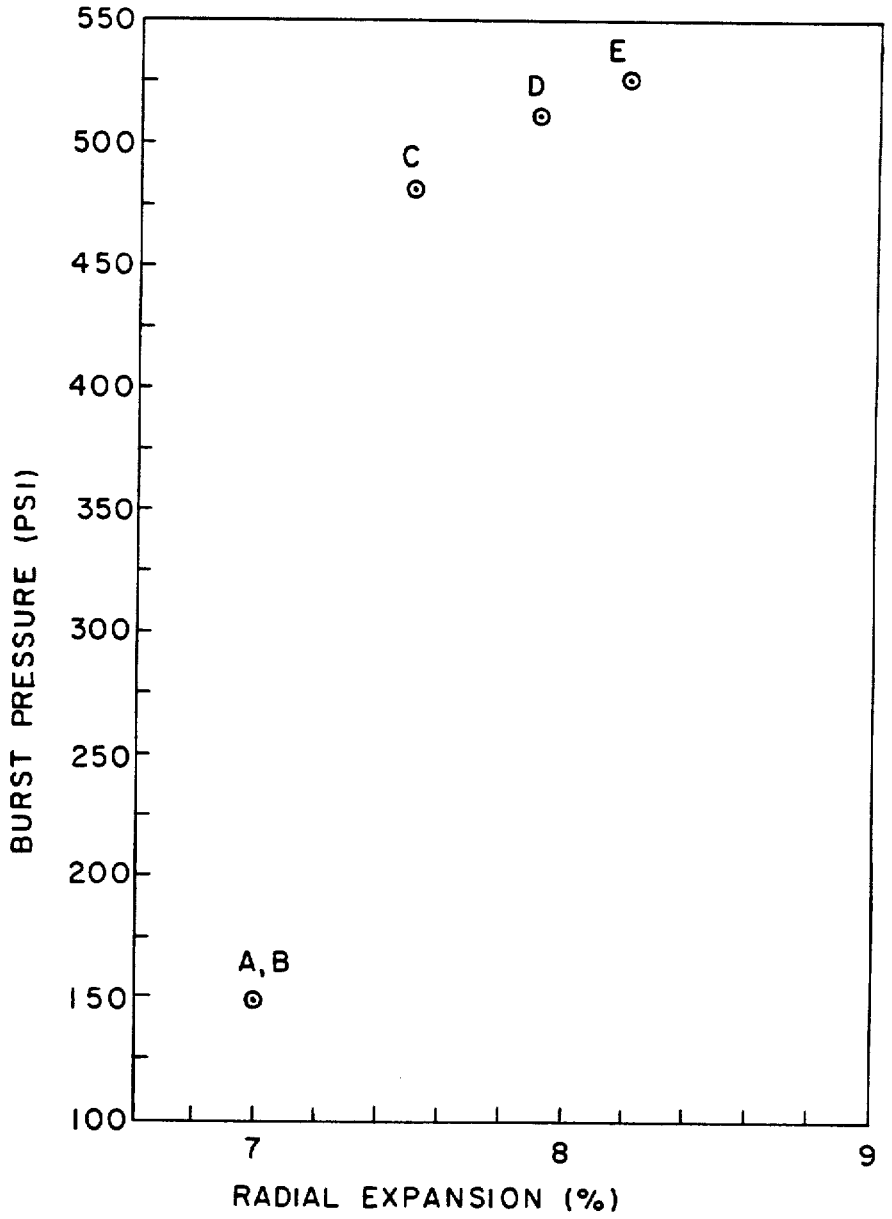
FIG. 2 shows the radial expansion (%) and burst pressure (psi) of three balloons of the invention (C, D and E) as compared to the radial expansion (%) and burst pressure (psi) of two balloons of the art (A and B).

The process comprises, at a temperature within the range extending from the second order transition temperature to the first order transition temperature, preferably at a temperature of 84°-99° C., more preferably 86°-96° C., drawing a polymeric, preferably a polyethylene terephthalate (PET) homopolyester, tubing, having a finite length ($L_1$) and an internal diameter (ID) which is preferably about one-half the outer diameter (OD), to a length ($L_2$) which is preferably 3 to 6 $L_1$, and thereafter expanding the drawn tubing of internal diameter $ID_1$ and outer diameter $OD_1$ by expanding means to an internal diameter ($ID_2$) which is preferably 6 to 8 ID and an outer diameter ($OD_2$) which is preferably about 3 to about 4 OD, followed by cooling the drawn and expanded tubing to less than its second order transition temperature, the balloon thus formed having a burst pressure, that is, the internal pressure at which the balloon bursts, of at least 200 psi (1.4 MPa) and a radial expansion beyond nominal inflated diameter of less than 5% at 200 psi (1.4 MPa), the preferred PET homopolyester, after conversion to tubing and balloon, having an intrinsic viscosity of 0.8 to 1.1. Such preferred tubing can be commonly formed by conventional extrusion techniques from PET homopolyester resin having an intrinsic viscocity of 1.0 to 1.3 and a density of 1.35 to 1.45. The balloon prepared by the process of this invention exhibits an unusual combination of film properties, such as toughness, flexibility and tensile strength. For example, the balloon of the invention exhibits a burst pressure of at least 200 psi (1.4 MPa), preferably at least 400 psi (2.8 MPa), more preferably at least 500 psi (3.4 MPa) at ambient temperature (20° C.). Moreover, the balloon of the invention exhibits a radial expansion beyond nominal inflated diameter of less than 5% when at a pressure of 200 psi (1.4 MPa) and less than 10% when at a pressure of 400 psi (2.8 MPa). FIG. 2 herein depicts burst pressure vs. radial expansion for two balloons (A and B) commonly available commercially and comprised of poly(vinyl chloride) and for three balloons (C, D and E) of the invention and comprised of PET homopolyester. Balloons A and C have nominal outer diameters of 3.7 mm; balloons B and D, 5.0 mm; and E, 6.0 mm. The wall thicknesses of A through E were, respectively, about 0.028, 0.038, 0.028, 0.038, and 0.045 mm. Radial expansion data for the balloons of the invention were calculated from the well known membrane equation and the ultimate elongation measured on flat film samples which were similarly biaxially oriented. Similar calculations were made for the poly(vinyl chloride) balloons except that published data were used for ultimate elongation. It can be seen that the burst pressures for the balloons of the invention are, respectively, 3.2, 3.4 and 3.5 times those for the balloons of the art. Regarding the burst pressure and radial expansion data reported herein, radial expansion is determined from the point at which the balloon is pressurized so as to be free of wrinkles, that is, after being inflated from its collapsed position to its nominal inflated diameter; a gas pressure of 75–100 psi (0.5–0.7 MPa) is required to reach this first expanded position with the PET homopolyester balloon of this invention. In general, a balloon of higher strength can be produced from the polymeric tubing by operating at high stretch ratios, that is, at the upper ends of the draw and expansion ratios. The balloon thus produced exhibits lower elongation, which is reflected in lower expansion values at a given inflation pressure, vis-a-vis a balloon produced under lower stretch conditions.

Intrinsic viscosity is determined herein by means of ANSI/ASTM D 2857-70 and density, by ASTM D 1505. Burst pressure is determined by a simple laboratory procedure whereby one end of the polymeric balloon is sealed off and a pressurized gas is introduced incrementally into the other end. The inflation pressure at which the balloon bursts at about 20° C. (ambient temperature) is referred to herein as the burst pressure.

Figure 1:
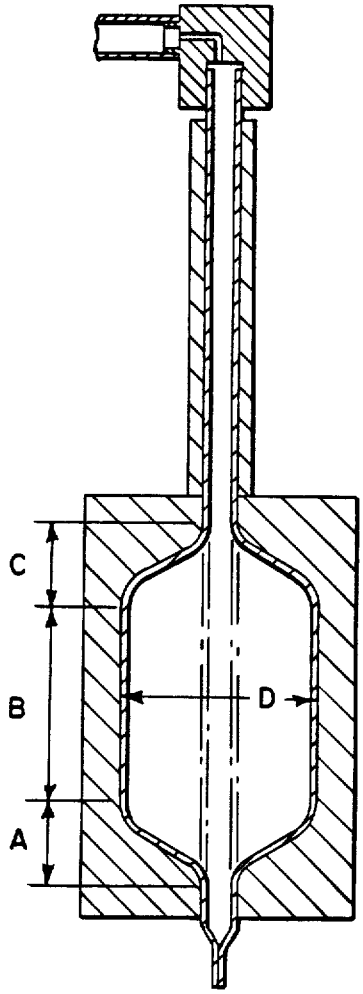
FIG. 1 is an elevation, in section, showing only the back half of the mold, balloon, tubing and attendant hardware of an apparatus which can be used to form the balloon of the invention from drawn polymeric tubing.

The process by which the balloon is prepared can be carried out in a conventional manner with conventional equipment using a specialized polymer as the material of fabrication. For example, the tubing of appropriate dimensions and of high molecular weight polymer is first drawn at a suitable temperature from a length $L_1$ to a length $L_2$. The drawn tubing is then expanded in a confining apparatus such as depicted in FIG. 1 which is a part of this specification. As shown therein one end of the tubing can be filled with a fluid under pressure during the expansion step of the process. The mold has a cavity of dimensions commensurate with the desired size of the balloon to be produced. The open end of the tubing is equipped with a suitable fitting so that a pressurized fluid can be introduced into the tubing. Any suitable fluid can be used to pressurize for inflation of drawn tubing, for example, a gas, such as nitrogen. If the tubing extends beyond the mold, such as shown in FIG. 1, use of a restraining means is preferred to maintain the dimensions of the tubing in the region outside the mold while pressure is being applied to the inside wall of the tubing. The restraining means can be of any material which is nondeformable under the tubing expansion conditions. After the drawn tubing is positioned in the mold, heat is applied to raise the tubing temperature. Similar temperatures can be used for both the drawing and expanding steps. A suitable temperature is the range extending from the second order transition temperature to the first order transition temperature of the polymer from which the tubing has been fabricated. For the PET homopolymer demonstrated herein, the preferred temperature is 84°–99° C., more preferably 86°–96° C. Although PET homopolymer is the only polymer demonstrated herein, it is to be understood that any high molecular weight polymer that can be extruded into tubing and then drawn and expanded in general accordance with the aforesaid process is operable, for example, a PET copolyester or even a nonpolyester polymer, provided the resultant balloon exhibits the desired film properties, such as toughness, flexibility and tensile strength. If the balloon is to be used in medical procedures involving contact with tissue, the polymeric material of construction should be tissue compatible.

It is critical to the invention that the intrinsic viscocity, a measure of the molecular weight of the polymer, be high. When the polymer is a homopolyester or copolyester PET resin, special, but well known, techniques may be employed to increase the molecular weight to the necessary level. The most commonly available PET homopolyester generally has an intrinsic viscosity of about 0.5 to 0.6, well below the requisite 1.0 to 1.3.

It will be understood by one skilled in the art that some adjustment in the draw and expansion ratios and the draw and expansion temperatures, as well as the intrinsic viscosity (molecular weight) and density, may be necessary to accommodate the difference in basic physical properties between the PET homopolyester exemplified herein and any other polymer used to fabricate the balloon.

One skilled in the art also will understand that, although the tubing drawing step is performed prior to the tubing expansion step, the latter can be performed immediately after the drawing of the tubing, or it can be performed at a later time. Moreover, although the drawing of the tubing can be performed using any suitable drawing means, it conveniently can be effected in the apparatus depicted in FIG. 1 so that the drawn tubing is already in place to perform the expansion. Because of the recovery characteristic of shaped polymeric structures which are drawn by the procedures used herein, it may be necessary to maintain axial tension on the drawn tubing during the expansion step. Consistent with all the above and readily understandable to one skilled in the art, the drawing and expansion steps can be performed at the same or at different temperatures. The desired temperature can be achieved by any suitable heat generating means. In actual experiments carried out herein with respect to the use of PET homopolyester, hot water was employed. Drawing of the tubing herein was achieved by using the weight of the mold.

A dilatation balloon catheter comprising the balloon of the invention can be fabricated by means of conventional techniques, and such a catheter can be used in accordance with accepted medical procedures.

Following is a description of a representative example of the invention. References to FIG. 1 in this example are for purpose of describing the cylinder dimensions A, B, C and D, since the embodiment of this example is only partially reflected in the figure, as will be obvious from the description. Tubing (1.5 mm OD$\times$0.75 mm ID) is inserted into a mold having a cavity shaped in the form of a cylinder, similar to that shown in FIG. 1, with ends which taper to smaller diameter cylinder slightly larger than the tubing OD. The diameter D of the cavity is about 5 mm and its length A+B+C, about 15 mm. The tubing is pinched off at the lower end of the mold, and weights are attached to the mold to produce the required axial drawing about (3×). The total weight of mold and weights is about 150 g. The weight of the assembly (mold, tubing and weights) is supported by the tubing which is fixed at its upper end by insertion into a tubing fitting. The assembly is inserted into a liquid medium at 87° C. and allowed to heat for about 1 minute. During that time axial orientation occurs because of the weight of the assembly in the heated liquid supported by the tubing. About 200 psi (1.4 MPa) of gas pressure is applied to the tubing, which radially orients the tubing (about 3.33×) in the mold cavity. This pressurization step lasts about two minutes, during which there is some additional axial draw. The assembly is cooled by immersion into a cold liquid, the pressure is released and the finished balloon is removed from the mold.

The process of this example was used to produce balloons having wall thicknesses of about 0.028–0.045 mm and burst strength of 480–525 psi (3.3–3.6 MPa), as showing in FIG. 2. The failure mode (on bursting) of such balloons is an elliptically shaped hole having its major axis substantially along the axial direction.

An alternate fabrication method and one more suitable for mass production would utilize a stationary mold having internal flow passages for hot and cold fluids. The tubing would be axially oriented to predetermined ratios by a stepper motor rather than by means of an attached weight. During the radial expansion phase, additional axial drawing may be required.

I claim:

1. High molecular weight, biaxially oriented, flexible polymeric balloon having a burst pressure of at least 200 psi (1.4 MPa) and a radial expansion of less than 5% at 200 psi (1.4 MPa).

2. Balloon of claim 1 having a burst pressure of at least 400 psi (2.8 MPa) and a radial expansion of less than 10% at 400 psi (2.8 MPa).

3. Balloon of claim 1 having a burst pressure of at least 500 psi (3.4 MPa) and a radial expansion of less than 10% at 500 psi (3.4 MPa).

4. Balloon of claim 3 wherein the polymer is a polyethylene terephthalate homopolyester having an intrinsic viscosity of 0.8 to 1.1.

5. Process for forming a high molecular weight, biaxially oriented, flexible polymeric balloon, the process comprising, at a temperature within the range extending from the second order transition temperature to the first order transition temperature, drawing a polymeric tubing having a finite length ($L_1$) and an internal diameter (ID) which is about one-half the outer diameter (OD) to a length ($L_2$) which is 3 to 6 $L_1$, and thereafter expanding the drawn tubing of internal diameter $ID_1$ and outer diameter $OD_1$ by expanding means to an internal diameter ($ID_2$) which is 6 to 8 ID and an outer diameter ($OD_2$) which is about 3 to 4 OD, following by cooling the drawn and expanded tubing to less than its second order transition temperature, said balloon thus formed having a burst pressure of at least 200 psi (1.4 MPa) and a radial expansion beyond nominal inflated diameter of less than 5% at 200 psi (1.4 MPa).

6. Process of claim 5 wherein the expanding means is pressurized fluid applied to the inside of the tubing.

7. Process of claim 6 wherein the pressurized fluid is a pressurized gas.

8. Process of claim 5 wherein the tubing is formed by extrusion of polyethylene terephthalate homopolyester resin having an intrinsic viscosity of 1.0 to 1.3 and a density of 1.35 to 1.45 and the balloon has a burst pressure of at least 400 psi (2.8 MPa).

9. Process of claim 8 wherein the temperature is in the range 84°-99° C.

10. Process of claim 8 wherein the temperature is in the range 86°-96° C.

11. Process of claim 8 wherein the tubing drawing temperature is different from the tubing expanding temperature.

12. Dilatation balloon catheter comprising the balloon of claim 1.

*13. Process for forming a high molecular weight, biaxially oriented, flexible polymeric balloon having a wall tensile strength of at least 31,714 psi (218.86 MPA), the process comprising, at a temperature within the range extending from the second order transition temperature to the first order transition temperature, drawing a polymeric tubing having a finite length ($L_1$) and an internal diameter (ID) to a length ($L_2$) which is 3 to 6 $L_1$, and thereafter expanding the drawn tubing of internal diameter ($ID_1$) and outer diameter ($OD_1$) by expanding means to an internal diameter ($ID_2$) which is 6 to 8 ID, followed by cooling the drawn and expanded tubing to less than its second order transition temperature.*

*14. Process of claim 13 wherein the balloon thus formed has a burst pressure of at least 200 psi (1.4 MPa).*

*15. Process of claim 13 wherein the expanding means is pressurized fluid applied to the inside of the tubing.*

*16. Process of claim 15 wherein the pressurized fluid is a pressurized gas.*

*17. Process of claim 13 wherein the polymeric tubing is formed by extrusion of polyethylene terephthalate homopolyester resin having an intrinsic viscosity of 1.0 to 1.3 and a density of 1.35 to 1.45.*

*18. Process of claim 13 wherein the tubing drawing temperature is different from the tubing expanding temperature.*

*19. Balloon produced by the process of claim 13.*

* * * * *